United States Patent
Boszczyk et al.

(10) Patent No.: US 12,390,251 B2
(45) Date of Patent: Aug. 19, 2025

(54) SPINAL FIXATION SYSTEM

(71) Applicant: NSPINE GMBH, Kolbermoor (DE)

(72) Inventors: Bronek Boszczyk, Kolbermoor (DE); Areena D'Souza, Kolbermoor (DE)

(73) Assignee: NSPINE GMBH, Kolbermoor (DE)

( * ) Notice: Subject to any disclaimer, the term of this patent is extended or adjusted under 35 U.S.C. 154(b) by 199 days.

(21) Appl. No.: 18/272,274

(22) PCT Filed: Jan. 12, 2022

(86) PCT No.: PCT/EP2022/050565
§ 371 (c)(1),
(2) Date: Jul. 13, 2023

(87) PCT Pub. No.: WO2022/152761
PCT Pub. Date: Jul. 21, 2022

(65) Prior Publication Data
US 2024/0065735 A1 Feb. 29, 2024

(30) Foreign Application Priority Data
Jan. 15, 2021 (EP) ..................................... 21151716

(51) Int. Cl.
*A61B 17/70* (2006.01)
(52) U.S. Cl.
CPC ................. *A61B 17/7053* (2013.01)
(58) Field of Classification Search
CPC .... A61B 17/7053; A61B 17/842; A61B 17/82
See application file for complete search history.

(56) References Cited

U.S. PATENT DOCUMENTS

| 9,775,651 B2 | 10/2017 | Le Couedic et al. |
| 2008/0208257 A1 * | 8/2008 | Matthys ............. A61B 17/7049 606/278 |

(Continued)

FOREIGN PATENT DOCUMENTS

| EP | 2 737 863 A2 | 6/2014 |
| EP | 3 082 630 B1 | 3/2018 |

(Continued)

OTHER PUBLICATIONS

Mar. 23, 2022 International Search Report issued in International Patent Application No. PCT/EP2022/050565.

(Continued)

*Primary Examiner* — Julianna N Harvey
(74) *Attorney, Agent, or Firm* — Oliff PLC

(57) ABSTRACT

A spinal fixation system for connecting a spinal vertebra to a rod, including a clamp and screw, the clamp having screw, band and rod channels. The rod channel extends through the clamp forming a passage for a rod, being open towards a lateral side and running approximately perpendicular to the screw channel. The band channel is adjacent to the screw channel and forms a passage for a flexible band. The screw channel has an internal screw thread for engagement with the screw to allow it to be advanced from a first band-locking position into a second rod-locking position. In the first position, the band channel is compressed to inhibit movement of the band with respect to the clamp, while allowing axial movement of the rod within the rod channel. In the second position, the rod channel is restricted to inhibit axial movement of the rod within the rod channel.

15 Claims, 2 Drawing Sheets

(56) References Cited

U.S. PATENT DOCUMENTS

| | | | |
|---|---|---|---|
| 2013/0268005 A1* | 10/2013 | Rezach | A61B 17/7053 606/279 |
| 2016/0242819 A1* | 8/2016 | Simpson | A61B 17/7053 |
| 2017/0086888 A1* | 3/2017 | Simpson | A61B 17/7053 |
| 2017/0086889 A1* | 3/2017 | Padilla | A61B 17/7053 |
| 2018/0110546 A1* | 4/2018 | Sournac | A61B 17/7053 |
| 2018/0153591 A1* | 6/2018 | Schafer | A61B 17/8869 |
| 2019/0029734 A1* | 1/2019 | Mickiewicz | A61B 17/7056 |
| 2021/0121204 A1* | 4/2021 | Murray | A61B 17/7032 |

FOREIGN PATENT DOCUMENTS

| | | | |
|---|---|---|---|
| FR | 2842724 A1 | 1/2004 | |
| FR | 2890850 A1 | 3/2007 | |

OTHER PUBLICATIONS

Mar. 23, 2022 Written Opinion of the International Searching Authority issued in International Patent Application No. PCT/EP2022/050565.

* cited by examiner

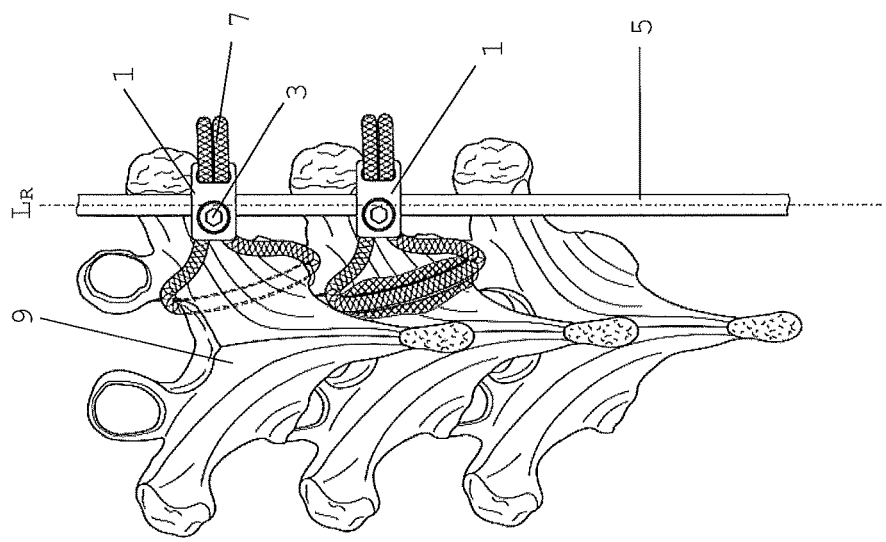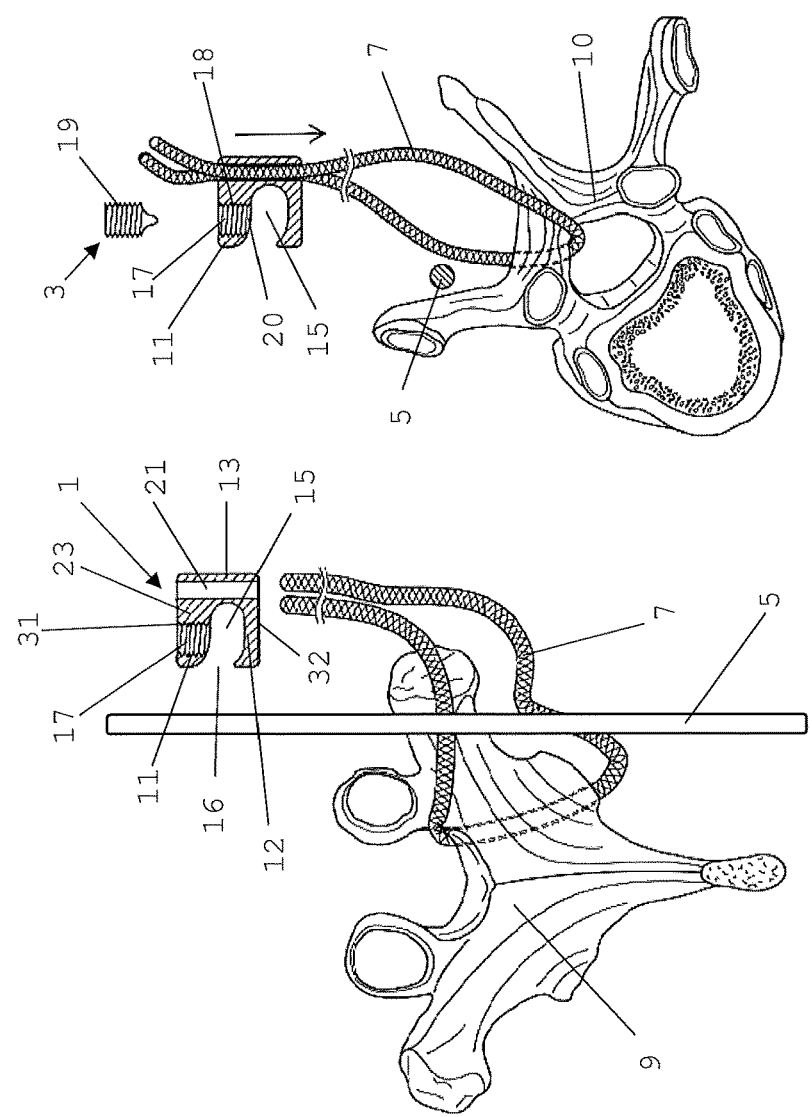

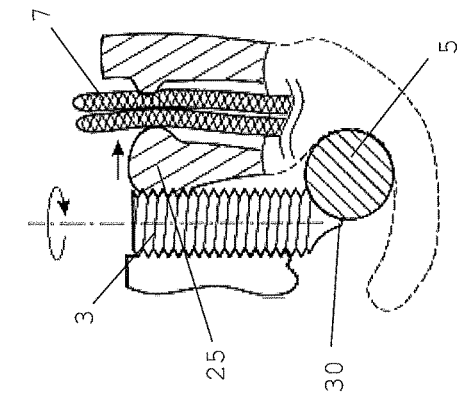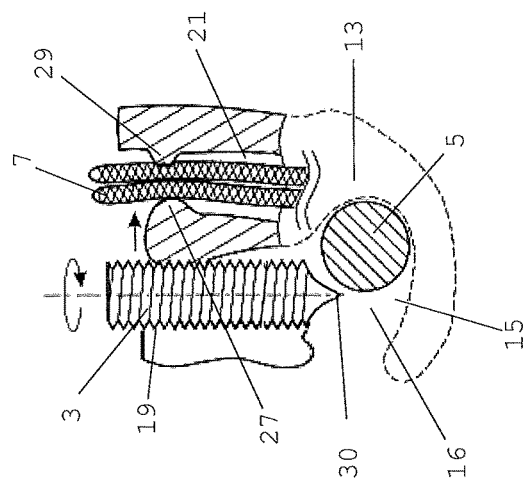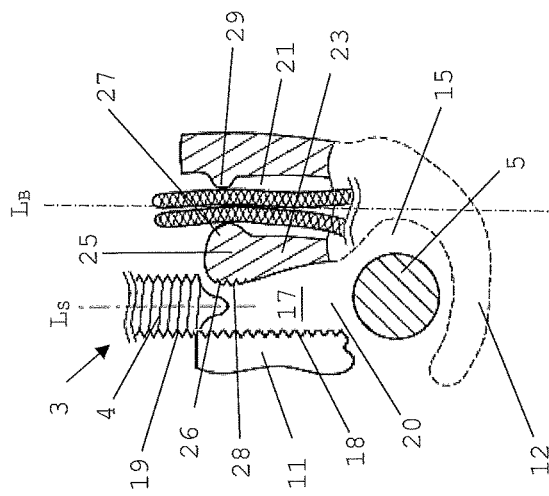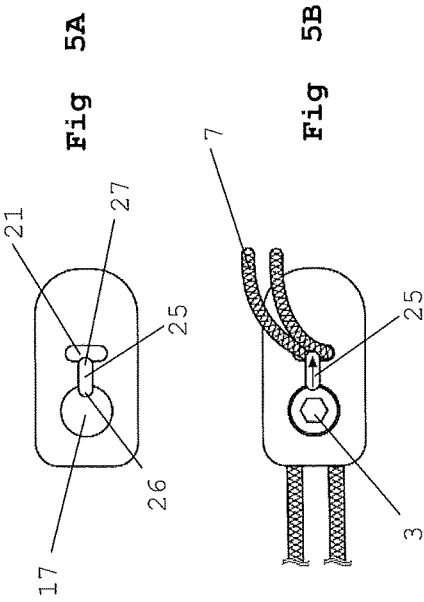

SPINAL FIXATION SYSTEM

The present invention relates to a spinal fixation system for attaching a spinal vertebra to a rod.

The present invention is particularly useful in the field of spinal deformity correction, i.e. if the vertebrae of a patient are not aligned correctly relative to each other with respect to the vertebral axis. In some places, the lateral edges of the vertebrae will therefore be on one side close to each other, and on the other side distant from each other.

In order to straighten the assembly, it is known to return to a substantially equivalent distance the lateral edges of the vertebrae on either side of the spine, by means of rods connecting together, or screws, which one inserts into the vertebrae themselves. Other systems use hooks—as e.g. disclosed in EP3082630B1, which are introduced along the spinal canal.

Such devices, however, have disadvantages.

The use of screws is first possible only if the vertebrae are in good condition and/or sufficiently wide at the fixation. Poor bone quality may for example be due to osteoporosis. Problems also arise in case of children or young adults, if the vertebrae are small and do not provide sufficient bone structure to allow safe fixation of a screw.

The use of hooks is very delicate because the operator must not touch the spinal cord on pain of paralysis of the patient.

In order to overcome these drawbacks, a system making it possible to avoid fixation screws or hooks has been proposed (e.g. FR 02 09 317 or FR 06 50 609). The system comprises a flexible tie for fixing of the vertebra on a linking piece, which is itself fixed to the straightening rod. Means for immobilizing the flexible tie by closure of the linking piece on the rod are provided.

Drawbacks of the above-described system are that articulation of the linking piece is necessary so as to permit lateral insertion of the rod and the flexible tie. The tie is moreover liable to slide over the vertebra and/or no longer grip it owing to the tensioning of other pieces linking to other vertebrae located in proximity and/or along the rod.

A further vertebral fixation device for holding a spinal vertebra to a rod is described in U.S. Pat. No. 9,775,651 B2. The device has a fixation element including a component of substantially U-shaped cross section with two branches. A loop is formed by a flexible band for connecting the vertebra to the component, and which passes through recesses provided in the branches. A removable sleeve is insertable in one of the branches and is intended to receive a screw. The sleeve includes a chamfered part designed to cooperate with the rod to compress the band between the rod and the bottom of the component upon insertion of the screw into the sleeve.

The system of U.S. Pat. No. 9,775,651 B1 has several drawbacks. On the one hand, it includes numerous components, which makes the system more difficult to assemble and install. On the other hand, upon tightening the screw, the device cannot be moved along the rod. Therefore, re-operation is necessary in case of growing children.

It is therefore an object of the present invention to provide a spinal fixation device which is particularly suited for use in children, avoids the use of bone screws and while allowing stable fixation of the spine to the device. Specifically, the spinal fixation device is adjustable to the special needs of children with respect to their softer bone structure and growth of their spine.

In line with the present invention a spinal fixation system for connecting a spinal vertebra to a rod is provided, said spinal fixation system comprising a clamp and a screw, preferably a set screw. The system is generally used in combination with a flexible band and a rod that are commonly used in the field of spinal fixation systems. During installation, the band may be tightened around the lamina of a misaligned vertebra and tensioned into a tightened position by a tensioning instrument.

The screw of the inventive spinal fixation system has a proximal head and a distal post with an outer thread and a free distal end. "Proximal" and "distal" are thereby used to designate opposite sides and with respect to the spine of a patient during installation of the spinal fixation system in a posterior access surgery. As such, the term proximal generally refers to the side facing the surgeon and thus away from the spine during installation, whereas distal refers to the side closer to the spine and more distant to the surgeon.

The clamp of the inventive system is preferably integrally formed, i.e. made as a single piece, and has a screw channel, a band channel and a rod channel. The rod channel extends along an axis through the clamp, which axis is in use often vertically oriented, and runs at least approximately perpendicular to the screw channel. The rod channel further forms a passage for receiving a rod and is open towards a lateral side.

The band channel is provided adjacent to the screw channel and forms a passage for receiving a flexible band. Preferably the band channel is sized to allow both ends of the band to pass through, i.e. when the band forms a loop, such that both ends can be brought together. Most preferably, the band channel, the screw channel and the rod channel are separated from one another. By "separate" it is meant, in the present context, that there is some material is interposed between the channels, such that they are not in contact with each other along their full length.

The screw channel runs at an angle, preferably essentially perpendicular, to the rod channel and has an internal screw thread for engagement with the outer thread of the screw to allow the screw to be advanced from a first band-locking position into a second rod-locking position. The two locking positions have distinct functions:

If the screw is in the first band-locking position, the cross-section of the band channel is compressed. The compression is such that movement of the band within the band channel with respect to the clamp is inhibited, preferably frictionally inhibited. Compression of the band channel does however not inhibit axial movement of the rod within the rod channel. Thus, if the screw is in the first band-locking position, the band can no longer move within the band channel, while axial movement of the rod in the rod channel is not restricted.

As will be explained further below, it is preferable that the screw positioning in this first band-locking position is such that it prevents the rod from disengaging in the first position while allowing movement of the clamp along the rod and while the band is generally already under tension. Said tension keeps the rod in place with respect to the vertebra(e) the band is attached to and also helps to keep rod within the rod channel. This concept is different from devices known in the art which either do not prevent the clamp from disengaging from the rod or do not allow for the band to remain under tension while allowing axial movement of the clamp along the rod.

On the other hand, if the screw is advanced into the second rod-locking position, a cross-section of the rod channel is restricted, such that axial movement of the rod within the rod channel—and thus movement of the clamp along the rod—is inhibited.

It is a key aspect of the present invention that a single screw is used to exert two locking functions: a) to lock the band into place with respect to the clamp, while allowing movement of the clamp along the rod, and b) to lock both the band and the rod into place with respect to the clamp.

The advantage of the inventive concept of using a single screw for fixation of either only the band or of the band and the rod with respect to the clamp will be explained in connection with a preferred example of implanting inventive spinal fixation system into a child body for correcting the position of a misaligned vertebra. In a surgical procedure, access to the spine of a patient is gained from the posterior side. Having freed the posterior side of the spine, one end of a flexible band is passed under the lamina of the misaligned vertebra, thereby forming a band loop. Both ends of the band are then passed through the clamp channel together. The rod is placed in proximity to the misaligned vertebra with the rod axis coaxial with the spinal axis. Then the clamp is moved along the band towards the spine with the lateral opening of the clamp facing the rod to allow lateral insertion of the rod into the rod channel. The clamp is advanced until it sits on the rod. The surgeon then places the band under tension by exerting a pulling force which draws the vertebra towards the clamp seated on the rod. By pulling the vertebra towards the rod the position of the vertebra can be corrected, such that it is aligned with the spinal axis along the rod. The surgeon then inserts a screw into the screw channel and advances the screw into the first band-locking position. This firmly connects the clamp and the band. Since the band is attached to the lamina of the vertebra and the tension of the band holds the clamp in place seated on the rod, the rod and the former misaligned vertebra are also firmly connected. Notably, said firm connection holds the vertebra and the rod at a predefined distance and prevents disengagement of the clamp and the rod. As long as the screw is in the first band-locking position, however, axial movement of the clamp along the rod is not inhibited. This is important as it allows the clamp to move along the rod as the spine of the patient grows and thus elongates. This is a significant advantage over fixation systems known in the art, which do not allow any movement of the components and thus require recurrent repositioning of the latter to allow spinal growth.

If the child is fully grown up, axial movement of the clamp along the rod is no longer necessary. At this point in time, the screw can be advanced into the second rod-locking position, in which both the band and the rod are prevented from moving with respect to the clamp. In other words: if the screw is in the second rod-locking position, any movement of the vertebra relative to the rod is inhibited.

The above example shows how the inventive system can be used in what is called passive and active growth modulation. In passive modulation the screw remains in the first band-locking position, thereby allowing the child to grow and the clamp to move along the rod as required by growth. In active modulation the band is tensioned, the screw locked in the first band-locking position and the clamp is then along the rod with force (e.g. by the surgeon in a distracting manoeuvres) along the rod in order to correct a spinal deformity. To keep the spine in the corrected state, the screw is then advanced into the second rod-locking position to fixate the position of the clamp on the rod. The clamp is generally repositioned, i.e. forcefully moved along the rod to exert a corrective force on the spine, every approximately 9 months while the child grows. The technique of active growth modulation is most appropriate when scoliosis curves are very stiff and require additional corrective force. As the screw of the inventive system can be alternated between the first band-locking position and the second rod-locking position, it can be used for both active and passive growth modulation as needed.

Apart from allowing spinal growth the inventive system provides the additional benefit that it uses a flexible band instead of screws or hooks for connecting a vertebra to the clamp (and thus the rod). This is particularly beneficial for use to correct the alignment of vertebrae of smaller size or with soft bone structure—which is both common in children.

In line with the present invention, advancing the screw to the first band-locking position causes compression of the band channel. This means that the cross-section of the band channel is reduced. In one embodiment the screw channel has a smaller diameter than the diameter of the screw post. It follows that the screw channel has to expand in order to allow insertion of the screw. By the screw channel and the band channel being provided adjacent to one another, expansion of the screw channel may directly lead to narrowing of the band channel.

In a preferred embodiment the clamp is integrally formed in one piece. In this way, there is no joint or gap into which bacteria, fluids, dirt etc. could enter, which allows a better cleaning. In addition, the provision of an integrally formed clamp facilitates the production of the latter and greatly increases the stability of the clamp itself. As a result, the production costs of the clamp can be lowered and the overall lifetime increased. A clamp that is integrally formed in one piece can be prepared for instance by means of a water stream or laser cutting procedure, 3D-printing or by injection moulding or machining.

In a preferred embodiment the screw channel and the band channel have a common partition wall section, said partition wall section including at least one deflection member that restricts the cross-section of the screw channel and is elastically deflected upon insertion of the screw, thereby causing widening of the screw channel and compression of the band channel.

The common wall section separates the screw channel and the band channel, in the sense of a partition wall. At least part of said common wall section is formed by a flexible deflection member. The cross-section of the screw channel is restricted by the at least one deflection member to an extent that the screw can only be inserted into the screw channel under deformation of the deflection member. Specifically, when inserting the screw into the screw channel, the outer surface of the screw post comes into contact with the deflection member, whereupon the latter is deflected in a direction radially away from the central longitudinal axis of the screw channel. The deflection member may thus be moved from a resting state into an engaging state by inserting the screw into the screw channel and advancing it into the first band-locking position. Thus, in general, the cross-section or diameter of the screw channel, which is in part defined by the deflection member, is at least slightly smaller than the diameter of the screw post when the at least one deflection member is in its resting position.

The deflection member can have any shape which enables it to be deflected radially outward of the screw channel, such that it restricts the cross-section of the adjacent band channel. For example, the deflection member may include a lug or a tongue that can be deflected upon insertion of the screw into the screw channel.

Preferably the deflection member includes an engagement surface, preferably in the area of the free end, which lies preferably flush with the inner surface of the band channel or may slightly protrude into the band channel if the deflection member is in its resting state. The engagement surface may be located on a protrusion, e.g. in the shape of a convex nub, wedge or tooth, formed on the deflection member and projecting therefrom in the direction towards the central longitudinal axis of the band channel (i.e. radially inwards into the space of the band channel). The purpose of such a protrusion is to decrease the cross-section of the band channel and to increase the compression force exerted by the deflection member on the band. Preferably, such a protrusion is formed at a free end of the deflection member that is located at a distance to the proximal opening of the band channel. The diameter of the screw channel and/or the band channel can remain constant, decrease or increase at various stages along its length. This means that it is also possible for the diameter of the channel to undergo a step change. Preferably however the diameter and cross-section of the screw channel and/or the band channel remains constant along its length.

Upon insertion of the screw into the screw channel and screwing it into the first band-locking position, the deflection member is deflected into its engaging state in which it is deflected radially away from the longitudinal axis of screw channel and thus radially towards the central longitudinal axis of the band channel. Upon deflection, the (preferably protruding) engagement surface will come into contact and frictionally engage with the band within the band channel, such that the band is pressed against the inner wall of the band channel opposite the deflection member and thereby locked in place.

In addition to a (first) protrusion provided on the deflection member—preferably laterally at the free end of the latter—as mentioned above, a further protrusion may be provided on the inner wall, specifically on the wall section facing said first protrusion. Upon deflection of the deflection member (i.e. when advancing the screw in the first band-locking position) the band will in this embodiment be compressed between the two protrusions, which significantly increases the local compression force exerted onto the band.

Preferably the common wall section between the band channel and the screw channel comprises a single deflection member. This simplifies the design and manufacture of the clamp. In such embodiments the deflection member of the clamp exerts a biasing spring force to press the band against the interior wall of the band passage when the screw is in the first band-locking position.

The spring characteristics, in particular the bending properties of the deflection member can be adjusted by altering the length, width and/or the thickness of the deflection member.

In a particularly preferred embodiment the screw channel is open at its bottom end and runs into the rod channel, whereby the dimensions of the screw channel and the screw being such that a free end of the screw protrudes into the rod channel when the screw is in the second rod-locking position. In this embodiment the free—distal—end of the screw protrudes into the rod channel and thereby the space within the channel, such that the rod can no longer move within the channel.

In a preferred embodiment advancing the screw into the second rod-locking position brings the free end of the screw into engagement with the rod and progressively compresses the rod against a wall of the rod channel. Advancing the screw into the second rod-locking position will thus press the rod against the inner wall of the rod channel in an area opposite the distal opening of the screw channel.

As mentioned above the screw post may be tapered, at least towards the distal end, with an increasing diameter in the proximal direction. In such embodiments, advancing the screw into the second rod-locking position may move the free distal end of the screw past the rod, such that a radially outer surface of the screw post comes into contact with the rod. Due to the tapered configuration of the screw post, advancing the screw will decrease the space available for the rod within the rod channel and exert compression on the rod until, when the screw is in the second rod-locking position, the rod is trapped between the screw post and the inner wall of the rod channel, such that relative movement of the rod with respect to the clamp is prohibited.

The screw channel may also be tapered in the distal direction, or it may have sections with different diameters. For instance, the screw may be provided with two adjoining portions of different cross-sections, in particular a first portion with a larger cross-section adjoined by a second portion with a smaller cross-section, and an intermediate shoulder formed on the screw. In this case, the screw channel may have two corresponding adjoining portions.

Alternatively, the screw post is fully cylindrical with an at least essentially constant diameter over its full length. This ensures that the stability and compression force that can be exerted by the screw on the rod is not reduced by a decreasing diameter of the screw post.

As regards the dimensions of the screw, it is preferred that the screw has a length in the range of 4 to 8 mm and a screw post with a diameter of 4 to 6 mm.

In addition, user information may be provided on the screw to assist the surgeon in identifying how far the screw must be advanced into the screw channel to sit in the first band-locking position and the second rod-locking position, respectively. Said user information is preferably provided by markings that indicate the required insertion depth.

With respect to the rod channel it is preferred that the free distance of the lateral opening is larger than the diameter of the rod. In this preferred embodiment it is further preferred that, in the first band-locking position, the free end of the screw protrudes into the lateral opening of the rod channel to hinder the rod from exiting the channel, while allowing axial movement of the rod within the rod channel. In other words, in the first band-locking position, the distal end of the screw protrudes into the rod channel and thereby reduces the lateral opening, such that the rod cannot escape the rod channel, yet without exerting compression on the rod. This embodiment is particularly beneficial when using the inventive system in active growth modulation. As explained further above, active growth modulation involves distraction manoeuvres to exert a corrective force on the spine in case of spinal deformity. The corrective/straightening manoeuvres are thus performed while the screw is in the first band-locking position, in which the band is already tensioned. The tensioned band on the one hand and the screw protruding into the lateral opening of the rod channel make sure that the clamp cannot dislodge from the rod, even if the clamp is forcefully moved along the rod to correct the curvature of the spine.

The screw channel and the band channel are preferably at least partly separate from one another. This means that they both preferably include at least a separate channel section. Separation of the two channels or channel sections is preferably provided by a partition wall, i.e. a common wall between the two channels or channel sections.

It is further preferred that the screw band channel has a channel section running essentially parallel to at least a channel section of the screw channel. By defining that at least a section of the screw channel and at least a section of the band channel is oriented in a parallel fashion, this also covers embodiments in which the full band channel and the full screw channel run essentially parallel to each other. The term "oriented" thereby always refers to the orientation of the central longitudinal axis of the respective channel or channel section.

Preferably, the above-mentioned channel sections of the screw channel and the band channel that are oriented at least essentially parallel to each other are both located at the proximal end of each channel. In other words; preferably at least the proximal end section of the screw channel and the proximal end section of the band channel run at least essentially parallel to one another.

The rod channel is said to be angled with respect to the screw channel. More preferably, the rod channel is oriented essentially perpendicular to at least the distal end section of the screw channel.

The configuration of the clamp is preferably such that both the screw channel and the band channel have a respective proximal aperture, while said proximal apertures of the screw channel and the band channel are positioned on a common side of the clamp. The aperture of the band channel is preferably sized to allow insertion of both ends of the flexible band simultaneously and is preferably slot-shaped.

In a particularly preferred embodiment both the screw channel and the band channel have a proximal end section that are separated via a common partition wall, such that each channel includes a separate proximal aperture in proximity to one other. In this embodiment at least the two proximal end sections of the screw channel and the band channel are preferably oriented essentially parallel to one another and the partition wall is in the area of the proximal end sections. The partition wall is preferably at least in part formed by or includes a flexible deflection member that can be deflected radially outwards with respect to the screw channel and thus radially inwards with respect to the band channel as described further above.

In a preferred embodiment the clamp has an at least substantially C- or U-shaped cross-section with two arms—a first extending arm and a second extending arm—connected via a bottom portion. The two arms and the bottom portion together form the rod channel. In this embodiment the screw channel is preferably formed in the first arm. The bottom portion preferably has a semi-cylindrical cross section, which is preferably at least substantially complementary to the cross-sectional shape of the rod. The band channel may also run through the first arm or at least in part through the bottom portion. Preferably, the band channel runs through the bottom portion of the clamp.

The two arms are preferably non-symmetrical with respect to a longitudinal plane. As mentioned, at least the screw channel preferably passes only through the first arm. Therefore, in this embodiment the first arm will look different from the second arm.

As one example of the two arms being symmetrically not identical it is preferred that the first arm has a larger cross-sectional width than the second arm. Again, this is particularly preferable if only the first arm comprises the screw channel. This does not exclude embodiments in which the screw channel and preferably also the band channel runs partly through the first arm and partly through the bottom portion.

If the screw channel only runs through the first arm it is further preferred that the second arm comprises a recess, which is situated opposite and facing the distal opening of the screw channel, said recess being of semi-cylindrical shape and sized to cooperate with an outer surface of the rod. Since the rod is preferably compressed into the recess upon tightening of the screw (advancing it into the second rod-locking position), the second arm—preferably both arms—are rigid, e.g. non flexible. This avoids elastic deformation of the clamp when the rod is compressed against the wall of the second arm.

With respect to the screw it is further preferred that the screw comprises an engagement surface at its free (distal) end, said engagement surface matching the outer contour of the rod and preferably comprises a conical section. The matching outer contour of the distal end of the screw and the surface of the rod enables a stable connection between the screw and the rod when the screw is advanced into the second rod-locking position. As such, immobilization of the clamp with respect to the rod is facilitated. In particular, a conical end section of the screw allows gliding movement of the clamp along the rod if the screw is in the first band-locking position, and further allows impinging the rod if the screw is advanced into the second rod-locking position.

The recess provided in the second arm described above and/or the engagement surface at the distal end of the screw may be contoured and/or roughened to facilitate a firm engagement with the rod. This roughening may be applied, for instance, by way of diamond plating, blasting, acid-etching etc. In general however, it is preferred that the rod and at least part of the end portion of the screw have polished surfaces that allow the clamp to glide easily along the rod as long as the screw is not advanced further than the first band-locking position.

If the screw comprises a conical end section at the free distal end, i.e. in the area of the tip, said conical section may comprise opposing surface areas with with different surface structures. For instance, one surface area may be smooth to allow gliding of the rod along said surface area if the screw is in the first band-locking position. An opposite second surface area may be provided with a roughened or textured surface. Said second surface area is intended to be in contact with the rod when the screw is in the second rod-locking position and the rod is thus compressed between the screw and the walls of the rod channel. To ensure correct placement of the mentioned surface areas in the first and second locking position, respectively, the screw can be inserted in a defined alignment with the inner screw thread provided in the screw channel of the clamp. This correct alignment could be indicated by markings, which may be provided on the surface of the screw head and on the surface of the clamp next to the proximal opening of the screw channel and which need to be aligned when inserting the screw into the screw channel.

Preferably the screw can be reversibly moved from the first band-locking position into the second rod-locking position and back. In general, the screw will only be moved into the second rod-locking position once the child has grown and axial displacement of the clamp along the rod is no longer necessary. However, should repositioning of the clamp be desired it is preferred that the screw can be screwed out of the screw channel to move it out of the second rod-locking position back into the first band-locking position—and even completely out of the screw channel if desired.

As already mentioned above, the band channel is preferably sized to allow simultaneous insertion of two opposite end portions of the flexible band brought together to form a loop. It is further preferred that the width of the band channel is more than the double width of the band, preferably at least three times the width of the band. This facilitates simultaneous insertion of the two ends of the band during surgery.

The size of the clamp and/or rod is such that it allows to withstand tensioning and alignment forces exerted by the band. The rod has preferably a diameter within the range of 3 mm to 6 mm. It may have a round outer contour or it may have a contoured shape, a rail shape for instance.

The materials used for the screw, the rod and/or the clamp must allow insertion thereof into the body of a patient. Preferred materials thus include stainless steel, titanium, cobalt chrome and carbon composites.

The rod channel is preferably sized to accommodate rods of different diameters. Since the cross-section of the rod channel can be restricted by the free end of the screw protruding thereinto, the diameter of the rod channel may be one or several millimetres larger than the diameter of the rod. In addition, the inner wall of the rod channel may be coated to minimize friction on the outer surface of the rod.

The invention will be explained in more detail in connection with the following non-limiting description made with reference to the accompanying drawings, in which:

FIG. 1 shows a perspective view of some components of a first embodiment of the inventive spinal fixation system, in which a clamp and a rod are placed in proximity to a vertebra and a band is wrapped around a lamina of the vertebra;

FIG. 2 shows a top view of the fixation system of FIG. 1, with the two free ends of the band inserted through a band channel in the clamp and a screw being positioned in proximity to the clamp in a non-locking position;

FIG. 3 shows a perspective view of a portion of a spine connected to a rod by means of two clamps and two screws of a second embodiment of the system according to the invention, whereby each clamp is sitting on the rod and connected to a respective vertebra by means of a laminar band;

FIG. 4A shows a cross-sectional view of a clamp and a screw of another embodiment of the inventive spinal fixation system, in which a rod is positioned within a rod channel and both ends of a band being inserted through a band channel of the clamp, with the screw being in a first band-locking position;

FIG. 4B shows the cross-sectional view of FIG. 4A, with the screw being in a first band-locking position;

FIG. 4C shows the cross-sectional view of FIG. 4A, with the screw being in a second rod-locking position;

FIG. 5A shows a top view of a clamp of a third embodiment of the inventive spinal fixation system, with a deflection member in a resting state; and FIG. 5B shows the top view of the clamp of FIG. 5A, with a band inserted in the band channel and a screw inserted in the screw channel, such that the deflection member is moved into a locking state.

In the following description, the same reference numbers will be used to denote the same elements. The terms "proximal" and "distal" are used relative to the surgeon, and not the operating field, i.e., not relative the patient.

The spinal fixation system of the present invention is used to aid in correcting the position and stabilization of one or more misaligned vertebra(e) during a posterior access surgery. As shown in FIGS. 1-3, the spinal fixation system includes a clamp 1 and a screw 3 (FIG. 2), in particular a set screw. The inventive spinal fixation system is generally used together with a rod 5 and a flexible band 7 that are both commonly used in this type of corrective spinal surgery. As shown in FIG. 3, two or more clamps 1 and respective screws 3 can be used to connect two or more vertebrae 9 to a single rod 5.

Since the clamp 1 is intended for placement at a desired implantation point adjacent to a vertebra 9, it is generally constructed of suitable biocompatible material, such as for example, stainless steel, cobalt chromium, or titanium.

The clamp is generally C- or U-shaped (when seen in cross-section) and has a proximal side 31 and a distal side 32. It includes two opposing arms 11, 12 that are connected via a bottom portion 13. The two arms 11, 12 and the bottom portion 13 together form a rod channel 15, which defines a passage for the rod along a longitudinal axis $L_R$ (see FIG. 3). The rod channel 15 is open on a lateral side, meaning that the two free ends of the two arms 11, 12 are spaced apart from one another and thus provide a lateral opening 16. Said lateral opening 16 is sized to allow lateral insertion of the rod 5 into the rod channel 15, when the rod 5 is oriented parallel to the longitudinal axis $L_R$ of the rod channel.

In the shown embodiments the two arms 11, 12 are not mirror symmetrical, since they have different cross-sectional shapes. One of the two arms—the first arm 11—comprises a screw channel 17 running therethrough. The screw channel 17 extends from the proximal side 31 of the clamp 1 to the distal side 32 and comprises an inner screw thread 18 that is adapted to engage with an outer screw thread 19 on the screw. The screw channel 17 runs along an axis $L_S$ (FIG. 4A), which is essentially perpendicular to the longitudinal axis $L_R$ of the rod channel. The screw channel runs into the rod channel, meaning that the distal end 20 of the screw channel 17 opens into the rod channel 15 (FIGS. 2 and 4A).

A band channel 21 is provided adjacent to the screw channel 17. In the embodiment shown in FIGS. 1 and 2, the screw channel runs through the bottom portion 13 of the clamp 1. The screw channel 17 and the band channel 21 each include a proximal channel section that is open towards the proximal side 31 of the clamp 1. It follows that both the proximal opening of the screw channel and the proximal opening of the band channel are located on a common side, namely the proximal side 31, of the clamp 1. Both proximal channel sections run parallel to one another and are separated by a common partition wall 23. Said common partition wall 23 includes a flexible deflection member 25 shaped as a tongue. The tongue 25 has a free end with a lateral portion 26 which protrudes into the screw channel 17 in its resting state (see FIGS. 4A and 5A). Opposite the lateral end portion 26, i.e. on the side facing the band channel 21, the tongue 25 includes a wedge-shaped protrusion 27 that protrudes from the surface of the tongue 25 towards the longitudinal center axis LB of the band channel 21. As shown in FIGS. 4A-4C, the wall of the band channel 21 opposite the common partition wall 23 may comprise a similar protrusion 29. The purpose of the protrusions 27, 29 and the deflection member 25 will be explained further below.

The installation of the inventive system starts with the surgeon attaching a laminar band 7 to a misaligned vertebra 9 and placing a rod 5 in proximity to said vertebra 9 (FIG. 1). The rod 5 is generally placed postern-lateral to the spine such that the rod axis is essentially coaxial to the spinal axis. The band 7 can be attached to the misaligned vertebra by wrapping the band 7 around the lamina 10 of said vertebra 9 (see FIGS. 1 and 2). In general, the surgeon will thread one end of the band from below around the lamina 10 with the aid of suitable tools known in the art. Both free ends of the band 7 are then brought together; such that the band forms a loop with the band looped around the lamina (shown in FIG. 1).

As shown in FIG. 2, both ends of the band 7 are then inserted through the band channel 21 of the clamp 1. The clamp 1 is then pushed along the band 7 towards the vertebra 9, with the lateral opening 16 facing the rod 5. This pushing movement is indicated by an arrow in FIG. 2. The clamp 1 is advanced until seated on the rod 5, i.e. until the rod 5 is held in the rod channel 15 (best seen in FIGS. 4A-4C). Since the band 7 is attached to the lamina 10 of the vertebra 9, the tension of the band 7 holds the clamp 1 safely seated on the rod 5 and prevents the rod 5 from moving out of the rod channel 15. The surgeon proceeds by placing the band 7 under tension by exerting a pulling force which draws the vertebra 9 towards the clamp 1 that is sitting on the rod 5. By this pulling action the position of the vertebra 9 can be corrected, such that it is aligned with the spinal axis along the rod 5. This corrected alignment is shown in FIG. 3. Tensioning of the band can involve the use of a tensioning instrument (not shown).

The fixation of the position of the components of the inventive system and the now correctly aligned vertebra will be explained in connection with FIGS. 4A-C: Having tensioned the band 7 and corrected the position of the former misaligned vertebra 9, the surgeon then inserts the screw 3 into the screw channel 17 and advances the screw 3 into a first band-locking position, shown in FIG. 4B. A first marking (not shown) may be provided on the screw post to indicate the depth of the screw to be set in the first band-locking position. Advancing of the screw within the screw channel 17 is preferably accomplished by engagement with a distal end of an engagement tool, such as a screwdriver (not shown), to rotate the screw 3 and thereby threading it into the screw channel 17. This is indicated by the circulating arrow in FIG. 4B.

Without the screw 3 inserted, the cross-section of the screw channel 17 is restricted by the walls of the screw channel. This is best seen in FIG. 4A. As mentioned above, there is a common partition wall 23 between the screw channel 17 and the band channel 21. It includes a flexible deflection member 25. Said flexible deflection member 25 is tongue-shaped and includes a free end with two lateral end portions: On the side facing the screw channel 17, the free end has a lateral end portion 26 with a screw thread 28, and on the side facing the band channel 21 the free end includes lateral end portion with a protrusion 27. If the deflection member 25 is in its resting position—shown in FIGS. 4A and 5A—the screw channel 17 has a smaller diameter than the diameter of the screw post 4. It follows that the screw channel 17 has to expand in order to allow insertion of the screw 3. By the screw channel 17 and the band channel 21 being provided adjacent to one another and being separated by the common partition wall 23, expansion of the screw channel 17 will directly lead to narrowing of the band channel 21, as shown in FIGS. 4B and 5B.

Advancing the screw 3 into the first band-locking position causes the deflection member 25, in particular the free end with the lateral end portion 26, to move radially outward of the screw channel 17—i.e. away from the longitudinal center axis $L_S$ of the screw channel (or at least of the proximal channel section thereof)—and thus radially inward into the band channel 21, as best seen in FIGS. 4B and 5B. This displacement of the deflection member 25 increases the cross-section of the screw channel 17, such that the screw 3 can be screwed-in further into the screw channel 17. At the same time, displacement of the deflection member 25 causes the lateral end portion with the protrusion 27 to protrude further into the band channel 21 and thus decrease the cross-section of the latter. Once the screw is set in the first band-locking position (FIG. 4B), the protrusion 27 provided laterally at the free end of the tongue 25 engages the band 7 and compresses the band 7 against the opposite wall section of the band channel 21. To increase the compression, the opposite wall section of the band channel 21 (i.e. the wall section opposite the protrusion 27) also comprises a protrusion 29 that protrudes from said wall section into the band channel 21. Upon deflection of the deflection member 25, the band is compressed between the protrusion 27 formed laterally at the free end of the deflection member 25 and the protrusion 29 formed on the opposite wall section of the band channel 21. Thereby, movement of the band 7 within the band channel 21 is inhibited and the clamp 1 can thus no longer move/slide along the band 7.

On the other hand, if the screw 3 is in the first band-locking position (FIG. 4B), axial movement of the clamp 1 along the rod 5 is still possible. This is important since it allows the clamp 1 to move along the rod 5 as the spine of the patient grows and thus elongates.

As shown in FIGS. 4A-4C, the proximal opening of the screw channel does not need to be planar. In the shown embodiment, the proximal end surface of the outermost part of the first arm 11 is higher than the proximal end surface of the partition wall 23. This facilitates insertion of the screw 3, since the screw thread 19 can first engage with the inner threads provided on the outer wall of the screw channel 17, prior to engaging the threads 28 on the lateral portion 26 of the deflection member 25 and thus deflecting the deflection member 25 towards the band channel 21.

As mentioned, the distal end 20 of the screw channel 17 opens into the rod channel 15. If the screw 3 is in the first band-locking position shown in FIG. 4B, the free end 30 of the screw 3 may protrude into the rod channel 15, yet only to a degree that axial movement of the rod 5 within the rod channel 15 is not inhibited. Preferably, however, in the first band-locking position, the free end 30 of the screw protrudes sufficiently far into the rod channel, such that it restricts the free distance defining the lateral opening 16 to prevent the rod 5 from moving out of the rod channel 15.

If the child is fully grown up, axial movement of the clamp 1 along the rod 5 is no longer necessary. At this point in time, the screw 3 can be advanced from the first band-locking position into a second rod-locking position, in which the free end 30 of the screw 3 engages with the rod and presses the rod 5 against the wall of the screw channel—as shown in FIG. 4C. How far the screw 3 needs to be advanced for reaching the second rod-locking position may be indicated by a second marking on the screw post (not shown), yet in general it is simply advanced until the proximal front end of the screw 3 lies flush with the proximal surface of the clamp 1. In this second rod-locking position, both the band 7 and the rod 5 are prevented from moving with respect to the clamp 1. In other words: if the screw 3 is in the second rod-locking position, any movement of the clamp 1 relative to the rod 5 and thus of the vertebra 9 relative to the rod 5 is inhibited.

To provide a secure engagement between the free end 30 of the screw 3 and the rod 5, the former has a conical end surface that serves as engagement surface and is shaped to match the outer shape of the rod 5. As such, the clamp 1 is allowed to glide along the rod 5 if the screw 3 is in the first band-locking position. By advancing the screw further into the second rod-locking position, the rod 5 is impinged by the conical end—as shown in FIG. 4C—and the clamp 1 can therefore no longer move with respect to the rod 5. The matching outer contour of the distal end 30 of the screw 3 and the outer surface of the rod 5 enables a stable connection between the screw 3 and the rod 5 when the screw 3 is advanced into the second rod-locking position shown in FIG. 4C.

By the conical shape of the free end 30 of the screw 3, advancing the screw 3 into the second rod-locking position may also indent the rod 5 and hereby deform the rod surface to lock the rod 5 and the clamp 1 securely together (not shown). To this end, metals of different strength and composition may be used for the screw 3 and the rod 5 to allow the screw 3 to indent the rod.

The outer surface of the clamp 1 may also include one or more flat surfaces which serve as engagement surfaces for an instrument to prevent clamp rotation while the screw is screwed into the screw channel to advance it into a first or second locking position.

As shown in FIG. 3, the surgeon may use more than one clamp 1 (and associated screw) to provide several anchoring points for the rod 5. While a single rod 5 can be used, each connection between a vertebra 9 and a respective clamp 1 will generally involve the use of a respective flexible band 7.

The invention claimed is:

1. A spinal fixation system for connecting a spinal vertebra to a rod, comprising:
   a clamp having a screw channel, a band channel and a rod channel; and
   a single screw having a distal post with an outer thread and a free distal end, wherein
   the rod channel extends along an axis through the clamp to form a passage for receiving a rod, the rod channel being open towards a lateral side through a lateral opening and extending perpendicular to the screw channel;
   the band channel is adjacent to the screw channel and forms a passage for receiving a flexible band;
   the screw channel extends at an angle to the rod channel and has an internal screw thread for engagement with the outer thread of the screw such that the screw is movable from a first band-locking position to a second rod-locking position,
   the screw being in the first band-locking position causes a cross-section of the band channel to be compressed to inhibit movement of the band within the band channel with respect to the clamp, while allowing axial movement of the rod within the rod channel, and
   the screw being in the second rod-locking position causes a cross-section of the rod channel to be restricted to inhibit axial movement of the rod within the rod channel.

2. The spinal fixation system according to claim 1, wherein the screw channel and the band channel have a common partition wall section, the partition wall section including at least one deflection member that is elastically deflected upon insertion of the screw into the screw channel, thereby causing widening of the screw channel and narrowing of the band channel.

3. The spinal fixation system according to claim 1, wherein
   the screw channel is open at a bottom end of the screw channel and runs into the rod channel, and
   dimensions of the screw channel and the screw are such that the free end of the screw protrudes into the rod channel when the screw is in the second rod-locking position.

4. The spinal fixation system according to claim 1, wherein
   a free distance of the lateral opening is larger than a diameter of the rod, and
   in the first band-locking position, the free end of the screw protrudes into the lateral opening of the rod channel to prevent the rod from exiting the rod channel, while allowing axial movement of the rod within the rod channel.

5. The spinal fixation system according to claim 1, wherein moving the screw into the second rod-locking position brings the free end of the screw into engagement with the rod and progressively compresses the rod against a wall of the rod channel.

6. The spinal fixation system according to claim 1, wherein the band channel has a channel section running parallel to at least a channel section of the screw channel.

7. The spinal fixation system according to claim 1, wherein a proximal aperture of the screw channel and a proximal aperture of the band channel are positioned on a common side of the clamp.

8. The spinal fixation system according to claim 1, wherein
   the clamp has a C- or U-shaped cross-section with an extending first arm and an extending second arm, both arms being connected via a bottom portion and together forming the rod channel, and
   the screw channel is formed in the first arm.

9. The spinal fixation system according to claim 8, wherein the two arms are non-symmetrical with respect to a longitudinal plane.

10. The spinal fixation system according to claim 8, wherein the first arm comprising the screw channel has a larger cross-sectional width than the second arm.

11. The spinal fixation system according to claim 8, wherein the second arm comprises a recess, which is positioned opposite and facing the screw channel, the recess being of semi-cylindrical shape and sized to cooperate with an outer surface of the rod.

12. The spinal fixation system according to claim 1, wherein the screw comprises an engagement surface at its free end, the engagement surface matching an outer contour of the rod.

13. The spinal fixation system according to claim 1, wherein the screw can be reversibly moved from the first band-locking position into the second rod-locking position and back.

14. The spinal fixation system according to claim 1, wherein the screw has a tapered section with a decreasing diameter towards the free distal end of the screw.

15. The spinal fixation system according to claim 1, wherein the band channel is sized to allow simultaneous insertion of two opposite end portions of the flexible band that are brought together to form a loop.

* * * * *